United States Patent [19]

Dea et al.

[11] 3,937,823
[45] Feb. 10, 1976

[54] TOPICAL ANTI-INFLAMMATORY COMPOSITIONS AND METHODS OF USE

[75] Inventors: Frank Jeng Dea, Newport Beach; Richard Allen Schroer, Silverado, both of Calif.

[73] Assignee: Nelson Research & Development Co., Irvine, Calif.

[22] Filed: Oct. 18, 1974

[21] Appl. No.: 515,906

[52] U.S. Cl. ............... 424/210; 424/211; 424/212; 424/217; 424/218; 424/224; 424/263
[51] Int. Cl.² .................. A61K 31/66; A61K 31/44
[58] Field of Search .......... 424/224, 263, 210, 211, 424/212, 217, 218

[56] References Cited
FOREIGN PATENTS OR APPLICATIONS
2,150,791   6/1973   France OTHER PUBLICATIONS
Goyer et al., Chem. Abst., Vol. 69, (1968), p. 94854f.

Primary Examiner—Sam Rosen
Attorney, Agent, or Firm—Martin A. Voet

[57] ABSTRACT

Compositions especially useful for treating inflammation topically in animals comprising an active compound having the structural formula

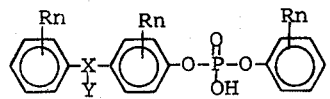

where R is H, lower alkyl, lower alkoxy, halogen, $CF_3$, $NO_2$, OH, CN, $COOR_1$,

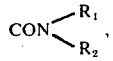

$NHCOR_1$ or $NR_1R_2$ where $R_1$ and $R_2$ are each selected from the group consisting of H and lower alkyl, R, $R_1$ and $R_2$ being the same or different, and $n$ is 0–5; and where X is an alkyl or alkenyl chain having 2–8 carbon atoms, one of which carbon atoms may be in the form of a carbonyl group, and Y is hydrogen, alkyl, aryl, aralkyl or aryl and aralkyl substituted with one or more R; and pharmaceutically acceptable salts thereof, together with a pharmaceutical carrier containing an effective amount of an active radical having the structural formula

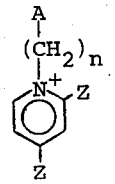

where $n$ is 1–4 and A is H or

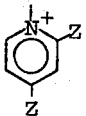

and Z is H or —CH=NOH or —CONHOH and one and only one Z in a heterocyclic ring is H.

14 Claims, No Drawings

TOPICAL ANTI-INFLAMMATORY COMPOSITIONS AND METHODS OF USE

BACKGROUND OF THE INVENTION

1. Field of the Invention

The present invention generally relates to novel compositions. More particularly, the present invention relates to novel compositions having enhanced anti-inflammatory activity.

2. Background of the Prior Art

French Patent Publication Nos. 2,150,791 and 2,150,792 generically disclose some of the active compounds set forth in the present application as being selective inhibitors of prostaglandin and slow reacting substance, a substance related to prostaglandin, having smooth muscle stimulatory activity. Topical use of these compounds is not possible, however, because of failure of these compounds to penetrate the skin in therapeutically effective amounts.

SUMMARY OF THE INVENTION

We have now discovered these compounds may be used topically if they are formulated in combination with an active radical which enhances the topical penetration of these active compounds.

The present invention therefore relates to a composition comprising an active compound having the structural formula

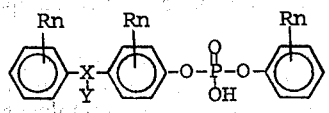

where R is selected from the group consisting of H, lower alkyl, lower alkoxy, halogen, $CF_3$, $NO_2$, OH, CN, $COOR_1$, $CONR_1R_2$, $NHCOR_1$ and $NR_1R_2$ where $R_1$ and $R_2$ are each selected from the group consisting of H and lower alkyl; R, $R_1$ and $R_2$ being the same or different, and $n$ is 0–5; and where X is selected from the group consisting of an alkyl or alkenyl chain having 2–8 carbon atoms, one of which carbon atoms may be in the form of a carbonyl group, and Y is selected from the group consisting of hydrogen, alkyl, aryl, aralkyl and aryl and aralkyl substituted with one or more R; and pharmaceutically acceptable salts thereof, together with a topical pharmaceutical carrier containing an effective amount of an active radical having the structural formula

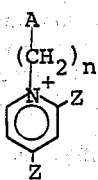

where $n$ is 1–4 and A is H or

and Z is H or —CH=NOH or —CONHOH and one and only one Z in a heterocyclic ring is H.

The method of the present invention utilizes the active compound together with a topical pharmaceutical carrier containing an effective amount of the active radical and relates to a method for enhancing the topical treatment of inflammation in animals including humans comprising applying topically to an animal an effective amount of the composition described above.

DETAILED DESCRIPTION OF THE INVENTION

The active compound has the formula

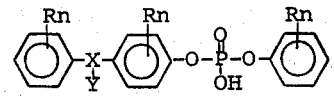

The active radical has the formula

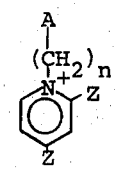

where $n$ is 1–4 and A is H or

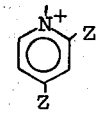

and Z is H or —CH=NOH or —CONHOH and one and only one Z in a heterocyclic ring is H.

The term "topical pharmaceutical carrier" as used herein and in the appended claims refers to those conventional pharmaceutically acceptable topical carriers including, but not limited to ointments, aqueous solutions, aerosols, suspensions or oil solutions. The proportion of the active compound in the composition may be widely varied. It is only necessary that the active ingredient of the invention be present in the carrier in sufficient concentration such that a conventional topical dosage form contains an effective amount of active compound.

The manner of application of the foregoing formulations is generally conventional: one to four times daily application of the topical formulation to the inflamed area by spraying or coating the inflamed area with a conventional amount of the selected topical formulation. The concentration of active compound which is to be used in the topical formulation ranges from about 0.1 to about 5% and preferably about 0.5 to about 3% by weight.

The term "pharmaceutically acceptable salt" as used herein and in the appended claims refers to those pharmaceutically acceptable salts conventionally employed, such as sodium potassium, ammonium, triethyl ammonium salts.

The term "topical treatment of inflammation" refers to the method whereby some or all of the signs and symptoms of inflammation are at least temporarily diminished or alleviated by topical application. Examples of conditions to which the foregoing method is applicable are sunburn, arthritis, eczema, dermatitis, uveitis, etc.

The term "animals" as used herein and in the appended claims refers generally to mammals and includes domesticated animals and humans.

Referring more particularly to the active compounds, X is an alkyl or alkenyl chain having 2-8 carbon atoms and preferably 2-4 carbon atoms, one of which carbon atoms may be in the form of a carbonyl group.

Y may be hydrogen or straight or branch chain alkyl radicals having 1-12 carbon atoms, such as, for example, methyl, ethyl, propyl, n-butyl, pentyl, hexyl, heptyl, etc.; aryl, such as, for example, phenyl, 1- and 2-naphthyl, biphenylyl, 2- or 3- thienyl, 2- or 3-benzo [b] thienyl, 2- or 3-furyl, 2- 3-indenyl, etc.; and aralkyl, such as, for example, benzyl, phenethyl, 1- and 2-naphthylmethyl, biphenylmethyl, 2- or 3-thienylmethyl, etc. Y may also be aryl or aralkyl substituted with one or more substituents R.

The substituent R is H, lower alkyl or lower alkoxy, that is, having 1-3 carbon atoms and preferably 1-2 carbon atoms, halogen and preferably —Br, —Cl or —F, $CF_3$, $NO_2$, OH, CN, $COOR_1$, $CONH_2$, $CONR_1R_2$, $NH_2$, $NHCOR_1$ or $NR_1R_2$ where $R_1$ and $R_2$ are H or lower alkyl, that is, having 1-3 carbon atoms and preferably 1-2 carbon atoms and $n$ is 0-5 R substituents. Further, R, $R_1$ and $R_2$ may be the same or different. Preferred R substituents are Br and Cl.

Preferred active compounds include those compounds of the foregoing structural formula wherein X is an alkyl or alkenyl chain having 3 carbon atoms, with or without a carbonyl group, R is H and Y is a benzyl group or benzyl group substituted with Br or Cl, preferably in the para position.

Generally, the active compounds disclosed herein may be made by methods known to those of skill in the art as exemplified by French Patent Publication Nos. 2,150,791 and 2,150,792.

Referring more particularly to the active radicals, these compounds are known in the art and can be made by conventional methods known to those of skill in the art of synthetic organic chemistry. Examples of active radicals include compounds having the formula

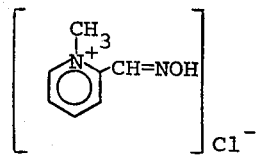

2-pyridine aldoxime-N-methyl chloride (2-PAM chloride);
compounds having the formula

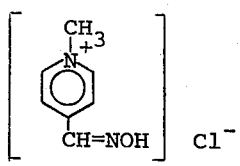

4-pyridine aldoxime-N-methyl chloride (4-PAM chloride);
compounds having the formula

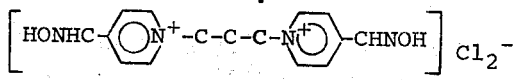

1,3-Bis-(pyridinium-4-aldoxime)-propane dichloride (TMB-4);
compounds having the formula

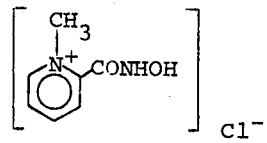

2-pyridine hydroxamic acid N-methyl chloride; and
compounds having the formula

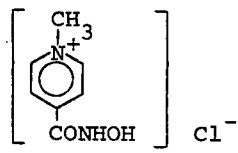

4-pyridine hydroxamic acid N-methyl chloride.

The foregoing radicals having been shown associated with a chloride salt, but other conventional salts including other halide salts, sulfate, methanesulfate, etc. may be used.

The foregoing active radicals significantly enhance the topical penetration of the active compounds described earlier.

The amount of active radical which may be used in the present invention is an amount effective to enhance topical penetration and ranges generally from about 0.5 to about 5% and preferably about 1 to about 3% by weiight of the final composition.

EXAMPLE I

A number of tests were performed comparing the topical anti-inflammatory activity of representative active compounds alone or in combination with effective amounts of active radical. The tests were performed on guinea pigs using a known animal inflammation model, namely the guinea pig UV-erythema test. In this test, a large area on the back of each guinea pig used in the test was shaved and depilitated. 18-24 hours after depilitation, each animal received a constant amount of irradiation by fixing the distance from the back of the animal to the light source (11 cm), the area of the surface to be irradiated (2 rings, 2 cm in diameter), the duration of the irradiation (30 seconds) and the intensity of irradiation emitted from the source (360 watt mercury vapor lamp with vycor glass heat filter). (Welhelmi and Domingez, Arch Internat. Pharmcodyn. 85, 129, 1951).

The weight of the animals was monitored closely, and the guinea pigs were randomized before each experiment.

After the exposure to radiation, each guinea pig was painted (using a Q-tip) with about 0.75 ml of the appropriate test solution. The solution was uniformly spread over the entire shaved area. Four animals were used for each test solution and/or concentration.

Because of the evaluation methods used in the test, two controls were used. One control involved treatment of animals with a placebo in order to be sure that normal inflammation developed and is designated "control (placebo)". A second control involved treatment of animals with a proven anti-inflammatory composition to ensure the test procedure was working properly and is designated "control (active)". The "control (active)" composition was a topical composition containing 3% Compound A and 3% 2-PAM chloride (see Table 2).

The development of the erythema was recorded at hourly intervals for six hours using a subjective grading system in which each irradiated spot was given a number (0,1,2,3) depending upon the severity of the reaction. The reaction corresponding to each number was defined as follows:

The topical composition used was 90% PEG (polyethylene glycol-300) and 10% water. The amount of chloride salt of active radical used was either equimolar (1×) to the first active compound or some multiple (2× etc) of the molar concentration of the active compound. The control always contained the highest concentration of the second active compound to be used in that test.

RESULTS

The results are tabulated in Table 1. Compound structures are given in Table 2. Each set of data represents an individual experiment. Active compounds are identified alphabetically.

Table 1

| Conditions | % Protection at | | | | | |
| --- | --- | --- | --- | --- | --- | --- |
| A. | 1 hour | 2 hrs | 3 hrs | 4 hrs | 5 hrs | 6 hrs |
| Control (placebo) | 0 | 0 | 0 | 0 | 0 | 0 |
| 1% Compound A | 20.6 | 33.3 | 16.7 | 8.3 | 8.3 | 8.3 |
| 1% Compound A + 1X 2-PAM | 0 | 27.6 | 29.0 | 4.3 | 0 | 0 |
| 3% Compound A | 0 | 27.6 | 25.0 | 12.3 | 8.3 | 0 |
| 3% Compound A + 1X 2-PAM | 79.4 | 72.0 | 50.0 | 29.0 | 12.3 | 8.3 |
| B. | | | | | | |
| Control (placebo) | 0 | 0 | 0 | 0 | 0 | 0 |
| Control (active) | 83.0 | 58.5 | 50.0 | 16.7 | 5.7 | 0 |
| 1% Compound B | 17.0 | 16.5 | 16.7 | 0 | 0 | 0 |
| 1% Compound B + 1X 2-PAM | 33.0 | 16.5 | 44.4 | 0 | 0 | 0 |
| 3% Compound B | 17.0 | 16.5 | 5.7 | 0 | 0 | 0 |
| 3% Compound B + 1X 2-PAM | 67.0 | 50.0 | 33.4 | 0 | 0 | 0 |
| C. | | | | | | |
| Control (placebo) | 0 | 0 | 0 | 0 | 0 | 0 |
| Control (active) | 85.1 | 59.9 | 45.7 | 21.0 | 8.3 | 0 |
| Compound C | 4.6 | 2.1 | 11.3 | 0 | 0 | 0 |
| 1% Compound C + 1X 2-PAM | 42.5 | 12.5 | 12.3 | 4.3 | 0 | 0 |
| 3% Compound C | 4.5 | 19.8 | 27.7 | 11.3 | 0 | 0 |
| 3% Compound C + 1X 2-PAM | 57.5 | 26.7 | 24.7 | 12.3 | 4.3 | 0 |
| D. | | | | | | |
| Control (placebo) | 0 | 0 | 0 | 0 | 0 | 0 |
| Control (active) | 42.6 | 56.5 | 37.7 | 12.3 | 0 | 0 |
| 1% Compound D | 13.8 | 18.5 | 12.3 | 0 | 0 | 0 |
| 1% Compound D + 1X 2-PAM | 24.1 | 25.0 | 16.7 | 0 | 0 | 0 |
| 3% Compound D | 27.6 | 30.5 | 20.3 | 4.3 | 0 | 0 |
| 3% Compound D + 1X 2-PAM | 0 | 25.0 | 29.0 | 8.3 | 0 | 0 |
| E. | | | | | | |
| Control (placebo) | 0 | 0 | 0 | 0 | 0 | 0 |
| Control (active) | 83.0 | 41.5 | 39.0 | 11.4 | 0 | 0 |
| 1% Compound E | 0 | 8.5 | 5.7 | 0 | 0 | 0 |
| 1% Compound E + 1X 2-PAM | 34.0 | 25.0 | 29.0 | 11.4 | 0 | 0 |
| 3% Compound E | 83.0 | 33.5 | 39.0 | 16.7 | 0 | 0 |
| 3% Compound E + 1X 2-PAM | 83.0 | 33.5 | 39.0 | 16.7 | 0 | 0 |
| F. | | | | | | |
| Control (placebo) | 0 | 0 | 0 | 0 | 0 | 0 |
| Control (active) | 62.1 | 42.9 | 45.5 | 17.8 | 13.2 | 0 |
| 1% Compound A + 1X 3-PAM | 25.0 | 0 | 4.4 | −4.2 | −4.2 | −4.2 |
| 3% Compound A + 1X 3-PAM | −13.0 | −21.7 | −9.1 | −4.2 | −4.2 | −4.2 |
| 1% Compound A + 1X 4-PAM | 50.0 | 57.2 | 45.5 | 26.1 | 13.2 | 13.2 |
| 3% Compound A + 1X 4-PAM | 50.0 | 71.4 | 49.8 | 17.7 | 13.2 | 13.2 |

0 — no redness
1 — reddish tint without distinct outline
2 — definite outline of reddish tint
3 — bright red The percent decrease of erythema in drug-treated animals compared to control animals treated with the same composition less the drug was calculated.

The foregoing tests demonstrate that 2-PAM chloride and 4-PAM chloride are comparable in their effect on enhancing penetration of the anti-inflammatory compounds, though they have no effect on inflammation themselves. Surprisingly, 3-PAM chloride, a structurally analogous compound, has no effect or even a negative effect on enhancing penetration of the anti-inflammatory compoundss.

Table 2

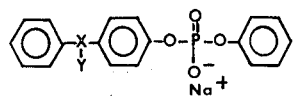

| Compound | X | Y |
|---|---|---|
| A | —CH₂—CH(Y)—C(=O)— | —CH₂—(C₆H₄)—Cl |
| B | —CH₂—CH(Y)—C(=O)— | H |
| C | —CH₂—CH(Y)—C(=O)— | —(CH₂)₃—CH₃ |
| D | —CH₂—(CH₂)₂—CH(Y)—C(=O)— | —CH₂—(C₆H₄)—Cl |
| E | —C(=O)—CH(Y)—CH₂— | —CH₂—(C₆H₄)—Br |
| F | —CH₂—CH(Y)—CH₂— | —CH₂—(C₆H₅) |

2-PAM chloride   3-PAM chloride   4-PAM chloride

EXAMPLE II

3% randomly tritiated Compound F (Table 2) was incorporated into a formulation containing 0 and 2× the molar concentration of 2-PAM respectively in propylene glycol. 0.5 cc of each formulation was placed in the reservoir chamber of a hairless mouse skin penetration model (Stoughton, R.B., Prog. Biol. Sc. in Relation to Dermatology, Cambridge University Press, Vol. 2, pp 263–274 (1964) while 10 cc of physiological buffer was placed in the receptor chamber. At various time intervals, aliquot samples were removed from the receptor chamber and analyzed for ³H-Compound F as an indication of its rate of penetration in the presence and absence of 2-PAM. Results in Tables 3 and 4 illustrate the advantageous effect of 2-PAM on Compound F resulting in a reduction of the lag time as well as an enhanced rate of penetration.

Table 3

| | Cumulative Amounts of Compound F Penetrated Through Hairless Mouse Skin (nanomoles per cm²) | | | | |
|---|---|---|---|---|---|
| | 40 | 50 | 60 | 70 | 80 hrs |
| 3% ³H-Compound F in PEG | 8.8 | 13.0 | 17.0 | 21.2 | 25.3 |
| 3% ³H-Compound F + 2X 2-PAM chloride in PEG | 14.8 | 19.2 | 23.7 | 28.2 | 32.6 |

Table 4

| | Lag time* (hours) |
|---|---|
| 3% ³H-Compound F in PEG | 19 |
| 3% ³H-Compound F + 2X 2-PAM chloride in PEG | 8 |

*Time requires for a minimum detectable amount of ³H-Compound F to penetrate through hairless mouse skin.

We claim:

1. A composition for treating inflammation comprising about 0.1 to about 5% of an active compound having the structural formula

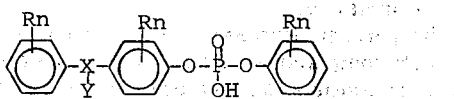

where R is selected from the group consisting of H, lower alkyl, lower alkoxy, halogen, $CF_3$, $NO_2$, OH, CN, $COOR_1$, $CONR_1R_2$, $NHCOR_1$ and $NR_1R_2$, $R_1$ and $R_2$ are each selected from the group consisting of H and lower alkyl, R, $R_1$ and $R_2$ being the same or different, and $n$ is 0–5; and where X is selected from the group consisting of an alkyl chain and an alkenyl chain having 2–8 carbon atoms, one of which carbon atoms may be in the form of a carbonyl group; and Y is selected from the group consisting of hydrogen, alkyl, aryl, aralkyl or aryl and aralkyl substituted with one or more R, and pharmaceutically acceptable salts thereof, together with a topical pharmaceutical carrier containing an effective amount of an active radical having the structural formula

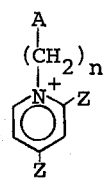

where $n$ is 1–4, A is selected from the group consisting of H and

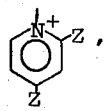

Z is selected from the group consisting of H, —CH=NOH and CONHOH where one and only one Z in each heterocyclic ring is H.

2. The composition of claim 1 where X is an alkyl chain having a 3 carbon atoms.

3. The composition of claim 2 where X contains a carbonyl group adjacent a ring.

4. The composition of claim 3 where Y is selected from the group consisting of

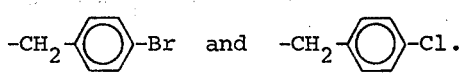

5. The composition of claim 4 wherein R is selected from the group consisting of H, halogen and $CF_3$ and $n$ is 1.

6. A method for treating inflammation in animals comprising applying topically to an animal an effective amount of the composition of claim 1.

7. A method for treating inflammation in animals comprising applying topically to an animal an effective amount of the composition of claim 4.

8. A composition for treating inflammation comprising about 0.5 to about 3% of an active compound having the structural formula

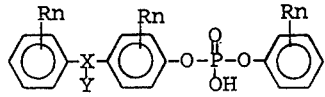

where X is selected from the group consisting of an alkyl chain and an alkenyl chain having 3 carbon atoms, one of which carbon atoms may be in the form of a carbonyl group; and Y is selected from the group consisting of

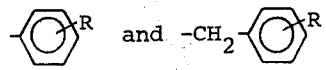

where R is selected from the group consisting of H, lower alkyl, lower alkoxy and halogen, and pharmaceutically acceptable salts thereof, together with a topical pharmaceutical carrier containing about 0.5 to about 5% of an active radical having the structural formula

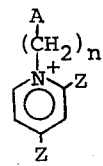

where $n$ is 1–4, A is selected from the group consisting of H and

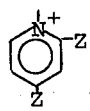

Z is selected from the group consisting of H, —CH=NOH and CONHOH where one and only one Z in each heterocyclic ring is H.

9. A method for treating inflammation in animals comprising applying topically to an animal an effective amount of a composition of claim 8.

10. A composition for treating inflammation comprising about 0.5 to about 3% of an active compound having the structural formula

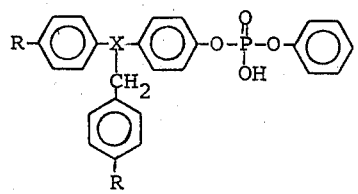

where X is selected from the group consisting of an alkyl chain and an alkenyl chain having 3 carbon atoms, one of which carbon atoms may be in the form of a carbonyl group; R is selected from the group consisting of H and halogen and pharmaceutically acceptable salts thereof, together with a topical pharmaceutical carrier containing about 0.5 to about 5% of an active radical having the structural formula

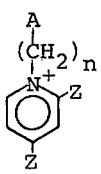

where *n* is 1–4, A is selected from the group consisting of H and

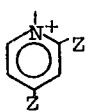

Z is selected from the group consisting of H, =CH=NOH and CONHOH where one and only one Z in each heterocyclic ring is H.

11. A composition for treating inflammation comprising about 0.5 to about 3% of α-(4-chlorobenzyl)-α-benzyl-4-hydroxyacetophenone phenyl hydrogen phosphoric acid or a pharmaceutically acceptable salt thereof, together with a topical pharmaceutical carrier containing about 0.5 to about 5% of a compound having the structural formula

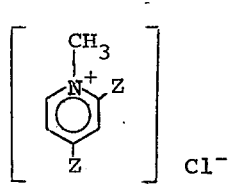

where one Z is H and one Z is —CH=NOH.

12. A composition for treating inflammation comprising about 0.5 to about 3% of an active compound having the structural formula

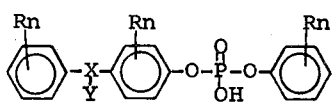

where X is selected from the group consisting of an alkyl chain and an alkenyl chain having 3 carbon atoms, one of which carbon atoms is in the form of a carbonyl group; and Y is selected from the group consisting of

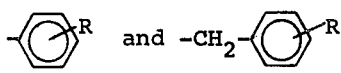

where R is selected from the group consisting of H, lower alkyl, lower alkoxy and halogen, and pharmaceutically acceptable salts thereof, together with a topical pharmaceutical carrier containing about 0.5 to about 5% of an active compound having the structural formula

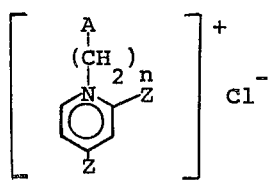

where *n* is 1–4, A is selected from the group consisting of H and

Z is selected from the group consisting of H, —CH=NOH CONHOH where one and only one Z in each heterocyclic ring is H.

13. A method for treating inflammation of the skin in animals comprising applying topically to an animal an effective amount of a composition of claim 12.

14. A composition for treating inflammation comprising about 0.5 to about 5% of an active compound having the structural formula

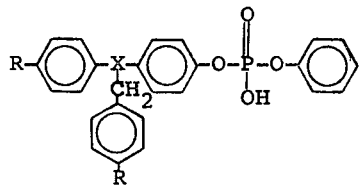

where X is selected from the group consisting of an alkyl chain and an alkenyl chain having 3 carbon atoms, one of which carbon atoms is in the form of a carbonyl group; R is selected from the group consisting of H and halogen and pharmaceutically acceptable salts thereof, together with a topical pharmaceutical carrier containing about 0.5 to about 5% of an active compound having the structural formula

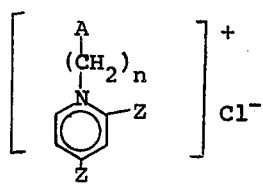

where *n* is 1–4, A is selected from the group consisting of H and

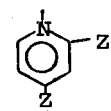

Z is selected from the group consisting of H, =CH=NOH and CONHOH where one and only one Z in each heterocyclic ring is H.

* * * * *